United States Patent
Wilzbach

(10) Patent No.: US 9,883,804 B2
(45) Date of Patent: Feb. 6, 2018

(54) METHOD AND DEVICE FOR EXAMINING A BIOLOGICAL TISSUE BY ANALYSING FLUORESCENCE RESPONSE TO ILLUMINATION AND FOR TREATING THE TISSUE

(71) Applicant: CARL ZEISS MEDITEC AG, Jena (DE)

(72) Inventor: Marco Wilzbach, Stuttgart (DE)

(73) Assignee: CARL ZEISS MEDITEC AG, Jena (DE)

( * ) Notice: Subject to any disclaimer, the term of this patent is extended or adjusted under 35 U.S.C. 154(b) by 191 days.

(21) Appl. No.: 14/376,191

(22) PCT Filed: Feb. 6, 2013

(86) PCT No.: PCT/EP2013/000355
§ 371 (c)(1),
(2) Date: Aug. 1, 2014

(87) PCT Pub. No.: WO2013/117330
PCT Pub. Date: Aug. 15, 2013

(65) Prior Publication Data
US 2015/0005596 A1    Jan. 1, 2015

Related U.S. Application Data

(60) Provisional application No. 61/595,177, filed on Feb. 6, 2012.

(30) Foreign Application Priority Data

Feb. 6, 2012    (DE) ................ 10 2012 002 086

(51) Int. Cl.
*A61B 5/00*    (2006.01)
*A61B 90/50*    (2016.01)

(52) U.S. Cl.
CPC .......... *A61B 5/0071* (2013.01); *A61B 5/0068* (2013.01); *A61B 5/0075* (2013.01);
(Continued)

(58) Field of Classification Search
CPC ... A61B 5/0059; A61B 5/0088; A61B 5/1455; A61B 5/14551; A61B 5/14532;
(Continued)

(56) References Cited

U.S. PATENT DOCUMENTS 3,449,571 A    6/1969    Hoerman et al.
3,657,537 A    4/1972    Wheeless, Jr. et al.
(Continued)

FOREIGN PATENT DOCUMENTS

DE    3210593 A1    10/1982
DE    3542167 A1    6/1987
(Continued)

*Primary Examiner* — Eric Winakur
*Assistant Examiner* — Chu Chuan (JJ) Liu
(74) *Attorney, Agent, or Firm* — Abel Law Group, LLP

(57) ABSTRACT

Method, and the associated device, for examining a biological tissue, in particular dental tissue or tooth enamel of one or several teeth, the method including the steps of taking into account at least the fluorescence of the tissue detected in a first wavelength range and the fluorescence of the tissue detected in a second wavelength range. The device can be a surgery microscope with one or several filters. The filters can be swiveled into or out the Illumination beam path or the optical path of the light source of the device.

29 Claims, 6 Drawing Sheets

(52) U.S. Cl.
CPC .......... *A61B 5/0077* (2013.01); *A61B 5/0088* (2013.01); *A61B 5/4836* (2013.01); *A61B 5/725* (2013.01); *A61B 90/50* (2016.02); *A61B 2090/502* (2016.02)

(58) Field of Classification Search
CPC ... A61B 5/0068; A61B 5/0071; A61B 5/0075; A61B 5/0077; A61B 5/4836; A61B 5/725
USPC ............ 600/309, 476, 310–344, 473; 433/29
See application file for complete search history.

(56) References Cited

U.S. PATENT DOCUMENTS

| | | | |
|---|---|---|---|
| 4,162,405 A | 7/1979 | Chance et al. | |
| 4,449,535 A | 5/1984 | Renault | |
| 4,479,499 A | 10/1984 | Alfano | |
| 4,556,057 A | 12/1985 | Hiruma et al. | |
| 4,833,332 A | 5/1989 | Robertson, Jr. et al. | |
| 4,852,987 A | 8/1989 | Lohmann | |
| 5,106,387 A | 4/1992 | Kittrell et al. | |
| 5,306,144 A | 4/1994 | Hibst et al. | |
| 5,341,805 A | 8/1994 | Stavridi et al. | |
| 5,419,323 A | 5/1995 | Kittrell et al. | |
| 5,452,723 A | 9/1995 | Wu et al. | |
| 5,456,252 A | 10/1995 | Vari et al. | |
| 5,503,559 A | 4/1996 | Vari | |
| 5,562,100 A | 10/1996 | Kittrell et al. | |
| 5,590,660 A | 1/1997 | MacAulay et al. | |
| 5,647,368 A | 7/1997 | Zeng et al. | |
| 5,701,902 A | 12/1997 | Vari et al. | |
| 5,749,830 A * | 5/1998 | Kaneko | A61B 1/00082 600/476 |
| 5,769,081 A | 6/1998 | Alfano et al. | |
| 5,800,165 A * | 9/1998 | Kirsch | A61B 1/24 433/29 |
| 5,827,190 A | 10/1998 | Palcic et al. | |
| 5,879,294 A | 3/1999 | Anderson et al. | |
| 5,914,247 A | 6/1999 | Casey et al. | |
| 5,983,125 A | 11/1999 | Alfano et al. | |
| 6,080,584 A | 6/2000 | Alfano et al. | |
| 6,091,985 A | 7/2000 | Alfano et al. | |
| 6,135,774 A * | 10/2000 | Hack | A61B 5/0088 433/29 |
| 6,603,552 B1 | 8/2003 | Cline et al. | |
| 6,631,289 B2 | 10/2003 | Alfano et al. | |
| 6,665,556 B1 * | 12/2003 | Alfano | A61B 1/063 600/473 |
| 6,813,009 B2 | 11/2004 | Riordan et al. | |
| 7,570,984 B2 | 8/2009 | Katsuda et al. | |
| 7,813,787 B2 | 10/2010 | de Josselin de Jong et al. | |
| 8,471,221 B2 | 6/2013 | Hennig | |
| 2002/0002337 A1 | 1/2002 | Alfano et al. | |
| 2003/0022126 A1 * | 1/2003 | Buchalla | A61B 5/0088 433/29 |
| 2003/0137649 A1 | 7/2003 | Riordan et al. | |
| 2003/0206301 A1 | 11/2003 | Cline et al. | |
| 2004/0023184 A1 | 2/2004 | de Josselin de Jong et al. | |
| 2004/0152987 A1 | 8/2004 | Haisch | |
| 2004/0196463 A1 | 10/2004 | Cline et al. | |
| 2005/0003323 A1 | 1/2005 | Katsuda et al. | |
| 2006/0240377 A1 | 10/2006 | de Josselin de Jong et al. | |
| 2007/0177650 A1 * | 8/2007 | Huston | G01J 5/0014 374/130 |
| 2007/0184402 A1 | 8/2007 | Boutoussov et al. | |
| 2008/0017787 A1 | 1/2008 | Okawa et al. | |
| 2009/0116029 A1 * | 5/2009 | Ohtera | G01J 3/02 356/456 |
| 2010/0219354 A1 | 9/2010 | Hennig | |

FOREIGN PATENT DOCUMENTS

| | | |
|---|---|---|
| DE | 69518915 T2 | 10/1995 |
| DE | 4427438 A1 | 2/1996 |
| DE | 10252313 A1 | 6/2004 |
| DE | 69724351 T2 | 6/2004 |
| DE | 102004001856 A1 | 7/2004 |
| DE | 102005061674 A1 | 7/2007 |
| DE | 102007047093 A1 | 4/2009 |
| DE | 102008011013 A1 | 9/2009 |
| DE | 102010037406 A1 | 6/2011 |
| EP | 0294996 A2 | 6/1988 |
| EP | 0935742 B1 | 2/1997 |
| EP | 1745736 A1 | 1/2007 |
| GB | 2126717 | 3/1984 |
| WO | 9006718 A1 | 6/1990 |
| WO | 2004032734 A1 | 4/2004 |
| WO | 2007079433 A2 | 7/2007 |

\* cited by examiner

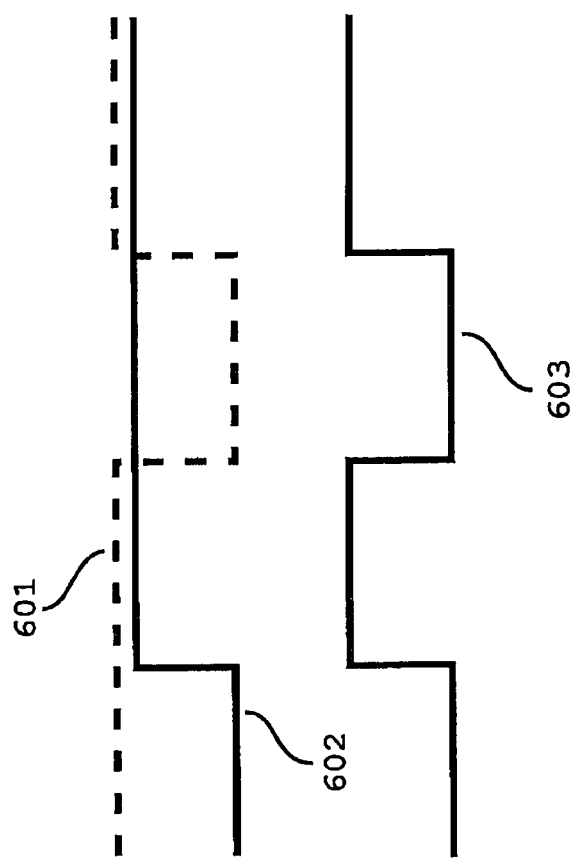

METHOD AND DEVICE FOR EXAMINING A BIOLOGICAL TISSUE BY ANALYSING FLUORESCENCE RESPONSE TO ILLUMINATION AND FOR TREATING THE TISSUE

BACKGROUND OF THE INVENTION

1. Field of the Invention

The present invention relates to a method and device for examining a biological tissue by analyzing its fluorescence response to illumination and for treating the tissue.

2. Discussion of Background Information

Practice discloses a plurality of methods for examining biological tissue. Some of these methods are based on the interpretation of a fluorescence beam or radiation, which is emitted by the examined tissue upon the stimulation or excitation thereof. Thereby, by way of example, the intensity or the wavelength of the fluorescence beam or luminescence are interpreted. Such a method is described in document U.S. Pat. No. 4,479,499.

It is an object of the present invention to provide a further method for examining biological tissue. In addition, it is aimed at presenting a suitable computing device, a corresponding monitoring system, a suitable treatment apparatus as well as a digital storage medium, a computer programme product and a computer programme.

SUMMARY OF THE INVENTION

The object according to the present invention is solved by a method, a computing device, a monitoring system, a treatment apparatus, and a set as set forth in the appended claims. The object according to the present invention is furthermore solved by a digital storage medium, a computer programme product and a computer programme, respectively, as also set forth in the appended claims.

The method for examining biological tissue according to the present invention may include taking into account at least one fluorescence of the tissue established or detected in a first wavelength range and a fluorescence of the tissue established or detected in a second wavelength range. Alternatively or in addition to taking into account as set forth supra the method may include measuring or assessing one fluorescence of the tissue established or detected in a first wavelength range and measuring or assessing a fluorescence of the tissue established or detected in a second wavelength range.

The computing device according to the present invention is suitable, programmed and/or configured for carrying out the method according to the present invention in at least one embodiment thereof, in particular in conjunction with corresponding facilities or devices and/or a corresponding monitoring or diagnosis system.

The monitoring or diagnosis system according to the present invention (also referred to infra as monitoring system) comprises at least one device for taking into account at least the fluorescence of a biological tissue established in a first wavelength range, in particular of a tooth or of a dental tissue, and of the fluorescence of the examined biological tissue established in a second wavelength range.

The treatment apparatus according to the present invention includes at least one computing device according to the present invention and/or at least one monitoring system according to the present invention or is connected therewith.

Also, the present invention relates to a set comprising or consisting of the monitoring system according to the present invention and the treatment apparatus according to the present invention.

A digital, particularly a non-volatile, storage medium according to the present invention, particularly in the form of a machine-readable data storage device, particularly in the form of a floppy disk, CD, DVD or EPROM, in particular with electronically or optically readable control signals, can cooperate with a programmable computer system in such a way as to trigger or prompt the mechanical steps of a method according to the present invention or the control or regulation of a device of an apparatus according to the present invention.

Thereby, all, some or a few of the mechanical or automatic implemented steps of the method according to the present invention can be triggered, prompted or executed.

A computer programme product according to the present invention includes a programme code stored on a machine-readable carrier for triggering, prompting or executing the mechanical steps of the method according to the present invention or for controlling or regulating a device of a system according to the present invention, when the computer programme product runs or is executed on a computer. According to the present invention a computer programme product can be understood as, for example, a computer programme which is stored on a storage device, an embedded system as a comprehensive system with a computer programme (e.g. an electronic device with a computer programme), a network of computer-implemented computer programmes (e.g. a client-server system, a cloud computing system, etc.), or a computer on which a computer product is loaded, executed, saved or developed.

A machine-readable carrier designates in certain embodiments of the present invention a carrier which contains software and/or hardware interpretable data or information. The carrier can be a floppy, a CD, a DVD, a USB stick, a flashcard, an SD card and the like.

A computer programme according to the present invention includes a programme code for triggering, executing or prompting the mechanical steps of the method according to the present invention or for controlling or regulating a device of a system according to the present invention, when the computer programme runs on a computer. A computer programme according to the present invention can be understood as, for example, a physical software product, which is ready for distribution and contains a computer program.

It is also the case with the computer programme product according to the present invention and the computer programme according to the present invention that all, some or a few of the mechanically or automatically executed steps of the method according to the present invention are triggered, prompted or executed by a device of an apparatus according to the present invention.

The present invention also relates to using the monitoring system according to the present invention together with the treatment apparatus according to the present invention.

Embodiments according to the present invention can include one or several of the features mentioned below. Embodiments according to the present invention are furthermore subject-matter of the dependent claims.

In all following explanations, the use of the expressions "can be" or "can have" are synonymous with "is preferably" or "has preferably" etc., and are to be understood as certain embodiments according to the present invention.

In certain embodiments according to the present invention, the biological tissue (below also in short: tissue) is a tissue of a patient. The patient can be sick or healthy. The patient can be a human being or an animal.

The examination of the tissue takes place in some embodiments in vivo, in others in vitro. In some embodiments according to the present invention, the biological tissue is a vital tissue, in others no vital tissue. In certain embodiments according to the present invention, the biological tissue is dental tissue or tooth enamel of one or several teeth.

In some embodiments according to the present invention, taking into account the fluorescence(s) determined in the first and/or the second wavelength range corresponds to considering or observing them, incorporating them in further steps—in particular mathematical steps—of the method according to the present invention, optically displaying, processing (in particular mathematically processing) or interpreting (or respectively (partial) steps thereof) the fluorescence(s) or at least one signal or value allocated to this or these, comparing at least one, or more, of the fluorescences with each other, or comparing at least one, or more, of the fluorescences or at least a signal or value allocated to said fluorescence(s) with at least one threshold value or with at least one reference range (e.g., for each fluorescence separately, or for a ratio thereof, or for the signal), and/or recording and/or storing by means of optical systems, in particular camera systems, basing a result or an assessment of said examined tissue, or any combinations thereof. In certain embodiments according to the present invention, taking into account includes at least one of the aforementioned ways of consideration.

In certain embodiments according to the present invention, fluorescence is understood as a tissue property, for example the amplitude, the intensity or the size of a radiation of the tissue obtained or observed in response to excitation by any or a pre-determined light (for example pre-determined regarding its wavelength(s)), in particular under or with particular wavelengths.

In some embodiments according to the present invention, fluorescence means a direct or indirect size or amplitude of a fluorescence radiation, but not the radiation itself.

In particular embodiments according to the present invention the established fluorescence means an observed or a measured fluorescence or a fluorescence established from known or measured or calculated or otherwise determined values or derived from tables or the like.

In certain embodiments according to the present invention a wavelength range is a range including a radiation (in particular an optical radiation) under one or several wavelengths. A wavelength can hence be defined by stating the length of their waves in nanometers (nm).

In certain embodiments according to the present invention, the method according to the present invention does not include making a diagnosis.

In some embodiments according to the present invention, the method does not include comparing the knowledge or information acquired by means of the present invention with patient data already present, in particular those of a collective.

In certain embodiments according to the present invention, the method exclusively relates to the recognition or the assessment of a physical property of the studied biological tissue.

In certain embodiments according to the present invention, the fluorescence of radiation is taken into account from exactly two wavelength ranges. Everything said herein in combination with two or more wavelength ranges relates in some embodiments according to the present invention to exactly two wavelength ranges.

In certain embodiments according to the present invention, the fluorescences of several wavelength ranges are taken into account simultaneously. In certain embodiments according to the present invention, simultaneously taking into account means or includes taking into account at the same time. In some embodiments according to the present invention, taking simultaneously into account means or includes creating and/or using a common signal resulting from the fluorescence of several wavelength ranges. Such a signal can have the form of a quotient or ratio or a pair of values.

In certain embodiments according to the present invention, taking into account consists of creating a common signal, which indicates a fluorescence qualitatively or quantitatively, or comprises such a step. Such a signal, or part-signal, may in some embodiments according to the present invention be gathered from or generated for each of the wavelength ranges independently from any other wavelength range. Such a signal may in certain embodiments according to the present invention be obtained by picking the highest intensity of all wavelengths of the wavelength range in question. Such a signal may in some embodiments according to the present invention be obtained by calculating an arithmetical average or an arithmetical median of the intensities of all considered wavelengths of the same wavelength range.

In particular embodiments according to the present invention, the first and/or second wavelength range comprises one wavelength.

In certain embodiments according to the present invention, the relative or the absolute intensities of the fluorescences in the at least two wavelength ranges are added to form a common signal or otherwise supplemented.

In some embodiments according to the present invention, the fluorescences of several wavelength ranges are taken into consideration to represent or display them simultaneously in an image, a film, etc.

In certain embodiments according to the present invention, taking into account the fluorescences of several wavelength ranges means or includes taking into consideration relative intensities of the fluorescences, optionally within the at least two wavelength ranges or between them, optionally related to reference values.

In some embodiments according to the present invention, the first wavelength range is or extends over a range from 500 nm to 520 nm or covers said range.

In certain embodiments according to the present invention, the second wavelength range is or extends over a range from 614 nm to 685 nm or covers said range.

In some embodiments according to the present invention, the first wavelength range is defined or determined as narrower than the second wavelength range. If the second wavelength range is for instance 20 nm (nanometer) wide, in which it includes wavelengths about between 620 nm and 640 nm, so the width of the first wavelength range is smaller than 20 nm.

In certain embodiments according to the present invention, the first and the second wavelength range do not overlap each other.

In some embodiments according to the present invention, none of the wavelength ranges taken into account overlaps any of the other wavelength ranges also taken into account.

In certain embodiments according to the present invention, the combination of the first wavelength range and of the second wavelength range includes a first pass band of 500 nm to 520 nm and a second pass band of 614 nm to 685 nm.

In other embodiments according to the present invention, the wavelengths of the first pass band range from 500 nm to 555 nm and those of the second pass band range from 614 nm to 675 nm.

Additional combinations according to the present invention of the first pass band range and second pass band range are as follows:
480-500 nm and 600-660 nm
485-505 nm and 620-690 nm
500-510 nm and 620-650 nm
550-560 nm and 610-650 nm In some embodiments according to the present invention, the lower cut-off or threshold wavelength of the first wavelength range equals or exceeds 460 nm.

In certain embodiments according to the present invention, the upper cut-off or threshold wavelength of the second wavelength range is not limited.

In some embodiments according to the present invention, the wavelength ranges located between the considered wavelength ranges are taken into account.

In certain embodiments according to the present invention, the upper limit of the first, lower wavelength range and the lower limit of the second, higher wavelength range are 5 nm or more apart from each other. In other embodiments according to the present invention, these two limits are 10 nm or more apart from each other. In further embodiments according to the present invention, these two limits are 60 nm or more apart from each other.

In certain embodiments according to the present invention, the method includes measuring the fluorescence radiation issued by the biological tissue, in at least two wavelengths or wavelength ranges.

In certain embodiments according to the present invention, the method includes measuring the fluorescence beam or radiation by using at least one double bandpass filter.

A double bandpass filter means in some embodiments according to the present invention a filter, which lets through radiation, in particular fluorescence radiation, from two predetermined wavelength ranges, but does not let through radiation of a wavelength which cannot be allocated to any one of two predetermined wavelength ranges.

Analogically to the double bandpass filter, in certain embodiments according to the present invention, a triple, quadruple, etc. bandpass filter can be implemented when more than two wavelength ranges are considered.

In some embodiments according to the present invention, when using the double bandpass filter as well as when using a triple, quadruple etc. bandpass filter, the filtering component and/or the filtering function is a complete, i.e. single, filter, or is realised by means of a complete filter. In other embodiments according to the present invention, the function of the double or multiple bandpass filter is divided into two or more components which are separate from each other. Components that are separate from each other can be incorporated parallel or alternately, possibly with a rapid changeover in the respective optical path (for example, the way along which light travels from an object or tissue under examination to a sensor, filter or lens, or the way along which light travels from a sensor, filter or lens to the eye of the observer, or vice versa).

In certain embodiments according to the present invention, the bandpass filter, in particular the double bandpass filter, is a combination of at least one pass filter, for instance, one long pass filter, and at least one notch filter, or includes such a combination.

A notch filter, also known as a Kerb-filter, can be provided as an electronic filter. Frequencies or wavelengths within a predetermined, for example a narrow wavelength or frequency range, can be filtered out by means of a notch filter. Notch filters can be provided as band elimination filters, also called frequency elimination or blocking filters or frequency traps.

In certain embodiments according to the present invention, the double or multiple bandpass filter is used for RGB (red-green-blue) colour channel separation. This way, a more efficient RGB channel separation of the colour camera utilised can be achieved. This method makes it possible to obtain, in particular with a QLF method (Quantitative Light-induced Fluorescence), advantageously better signal qualities.

In certain embodiments according to the present invention, the observation filter in use (for example provided as a double bandpass filter) and/or the illumination filter in use are non-digital filters. Similarly, in certain embodiments the present invention is based on non-digitally filtering, taking into account non-digitally analysis, non-digital processing and/or non-digital assessment, and so on, or includes them.

The observation filter utilised, in particular the bandpass filter, can be an optical filter. In certain embodiments according to the present invention, the observation filter is a dichroic filter.

In certain embodiments according to the present invention, the monitoring system can be arranged or configured to perform or to allow a so-called "boost"-function. A boost function is in certain embodiments according to the present invention an upward regulation which takes place particularly as a short-time, in particular time-limited upward regulation, an increase or amplification of the illumination of the emitted light, or (respectively) of the intensity thereof, in particular over a predetermined time period.

Some embodiments according to the present invention provide for the activation of such a boost function when pivoting the filter, for instance the illumination filter or the observation filter, into a radiation or observation path, or the activation of a corresponding or predetermined filter position. Alternatively, such a boost function starts when a further or another component of the monitoring system is being activated, for example a mechanically movable component, a switch or the like.

In certain embodiments according to the present invention, the boost function, as described supra, is activated automatically and/or triggered by a pivoting motion, as illustrated above, of at least one of the filters or when operating a further or another component of the monitoring system.

In some embodiments according to the present invention, the method includes illuminating the biological tissue by illumination waves in order to obtain a fluorescence radiation. Other embodiments according to the present invention do not include such an illumination.

In some embodiments according to the present invention, the method includes illuminating the biological tissue by illumination waves which have a wavelength or wavelengths that are smaller than the wavelength(s) of the first wavelength range.

In certain embodiments according to the present invention, the method includes illuminating with waves of a wavelength range comprising wavelengths between 350 nm and 500 nm, in particular between 370 nm and 440 nm, in particular between 39.8 nm and 437 nm, or being limited thereto.

In certain embodiments according to the present invention, the illumination includes waves of a wavelength range which is arranged symmetrically with regard to 405 nm. By way of example, the wavelength range of the illumination waves includes wavelengths from 370 nm to 440 nm.

In some embodiments according to the present invention, the method includes illuminating the biological tissue (exclusively or in complement thereto) by means of one or of several light-emitting diodes (LED) and/or by means of a laser.

In certain embodiments according to the present invention, the computing device is connected to control or regulation units, in particular of a treatment apparatus, in signal communication, or includes such elements.

The apparatuses according to the present invention include in certain embodiments according to the present invention devices or means for performing some or all of the method steps mentioned herein.

In certain embodiments according to the present invention, the devices mentioned in this context or required for their performance are means, devices, etc. which are not only suitable for the respective stated use, but also explicitly provided, configured, programmed, etc. to that end.

In some embodiments according to the present invention, the monitoring system includes at least one of a device for measuring, an (observation or illumination) filter or a filter arrangement, which (completely or in at least one section thereof) is arranged such that it can be moved or transferred, preferably by hand or by actuating or pushing a foot pedal, for example, by the observer who might be the dentist and, for example, via a lever, handle, a feeder, a pusher or any other filter moving device, from a first position, in which it is not arranged in an optical path (or in the respective optical path in question), into a second position, in which it is arranged in the optical path. It may be arranged to be pushed, pivoted, rotated, inserted, etc., or for a transfer.

In certain embodiments according to the present invention, the monitoring system is a camera for continuing image acquisition, for instance for creating a film, or includes such an element. In other embodiments according to the present invention, it does not.

In some embodiments according to the present invention, the monitoring system includes a device for superimposing white light (for example, the light having the color of light that contains all of the wavelengths of the visible spectrum without absorption) onto an optical representation or illustration of said at least one fluorescence of the tissue established in a first wavelength range and of a fluorescence of the tissue established in a second wavelength range.

In particular embodiments according to the present invention, the monitoring system or the treatment apparatus includes a handle or a hand-held device, in or on which a device for illuminating the biological tissue by illumination waves for obtaining a fluorescence radiation is provided.

In certain embodiments according to the present invention, the monitoring system or the treatment apparatus comprises a device for illuminating the biological tissue by means of illumination waves for obtaining or triggering a fluorescence radiation. This device for illuminating is in some embodiments according to the present invention designed or arranged to be movable with respect to further sections of the treatment apparatus or the monitoring system, or both, while using the monitoring system or the treatment apparatus. The further sections may include one or more of the illumination filter, the observation filter, the lever for moving a filter into an optical path, and the like.

The device for illuminating is designed in some embodiments according to the present invention as illumination fibres, light guide, optical conductor, or fibre optics.

In some embodiments according to the present invention, the monitoring system is a microscope, an operational microscope, a surgery microscope, a dental microscope, a head-carried or head-set microscope, magnifying glasses, a digital microscope or the like, or comprises such a device or such devices. In certain embodiments according to the present invention the aforementioned devices are optical devices and/or light devices, such as light microscopes, light magnifying glasses and the like. In some embodiments according to the present invention the aforementioned devices do not comprise a wavelength division multiplexer (WDM) and/or a charged-coupled device (CCD), or consist thereof. In particular embodiments according to the present invention the aforementioned devices are not a digital camera or not interconnected with a digital camera or both.

In certain embodiments according to the present invention the treatment apparatus is a device for treating the biological tissue. It can, in particular, be a dental drill or a device for removing dental calculus, stains or tartar, or comprise such a device or such devices.

The treatment apparatus comprises in some embodiments according to the present invention a device for automatic interruption of the treatment. The device may interrupt the treatment depending on or on the basis of the at least one fluorescence of the tissue established in the first wavelength range and/or the fluorescence of the tissue established in the second wavelength range. This takes place, for instance, after the emitted fluorescence(s) and/or the signal derived therefrom has been compared with a reference or threshold value or with a reference or threshold range, or the like.

All advantages achievable by the method according to the present invention can also be attained in certain embodiments according to the present invention with each of the devices and apparatuses according to the present invention. This is also true of some embodiments according to the present invention for the digital storage medium according to the present invention, the computer programme product according to the present invention and also the computer programme according to the present invention.

Methods for exciting tissue by light in order to make it emit a fluorescence beam and methods for analysing the measured fluorescence are known to the skilled person from, for example, the U.S. Pat. No. 5,503,559 to Sandor G. Vari, and from the German patent application file for Ferton Holding S. A., laid open under DE 10 2007 047 093 A1, each of which is expressly incorporated herein in its entirety by reference thereto.

In certain embodiments according to the present invention, the set comprises or consists of the monitoring system according to the present invention and the treatment apparatus according to the present invention, wherein the monitoring system comprises the observation filter and wherein the treatment apparatus comprises the device (or source) for illuminating the biological tissue. In some of those embodiments, the device (or source) for illuminating the biological tissue is comprised in a hand-held tool, for example a dental drill.

Some, a few or certain embodiments according to the present invention present one, some or all of the following and/or the aforementioned advantages:

An advantage of some embodiments according to the present invention is that a signal can be generated which is strong enough and/or interpretable enough when taking account or considering the fluorescence radiation of several wavelength ranges, so as to represent tissue properties such as tooth decay or caries, even, partially, in continuous display such as on a film. In this aspect, the procedure according to the present invention may advantageously differ from the state of the art. This holds true, first of all, if, as usual in the prior art, only fluorescence radiation of one wavelength range is taken into account. In certain embodiments according to the present invention, it can hence be possible for the user or the dentist to advantageously detect tooth decay or caries as red areas in an otherwise green fluorescent environment in the healthy tooth, optically with prominence and, hence, in an easy way.

Furthermore, to detect a certain tissue property such as tooth decay or caries, the user does not need any camera and/or, in particular, more costly illumination of the tissue or tooth. The observation can take place by means of the human eye alone without using digital camera technique. Consequently, the tissue or the tooth can be assessed by means of a surgery microscope or treatment apparatus.

Moreover, it is advantageous to be able in certain embodiments according to the present invention to consider and/or to interpret the fluorescences in question in the course of a treatment of the tissue, for example the tooth treatment. In this aspect, the present invention differs advantageously in the corresponding embodiments from the disclosure of, by way of example, the document U.S. Pat. No. 4,447,499 which is mentioned in the introduction of this specification.

A further advantage of some embodiments according to the present invention is that a treatment of the tissue, for example a tooth, need not be interrupted for controlling the tissue properties of the tooth. Rather, the treatment may unfurl under permanent "live" control of the status of the tooth by the treating dentist. With certain embodiments according to the present invention, it is not necessary to change instruments between the treatment apparatus and the monitoring system and vice versa.

Due to or by means of the selection of the width of the pass band ranges and/or of the spacing of the fluorescence radiation taken into account from different wavelength ranges or filter pass band ranges, the sensitivity and the discrimination capacity of the eye can be used advantageously. The sensitivity as well as the discrimination capacity are established optimally with the aforementioned wavelength ranges, in particular due to their width and position in the radiation spectrum on the one hand as well as relative to one another on the other hand.

If, like in some embodiments according to the present invention, the width of a red fluorescing wavelength range is found to be larger than the width of a green fluorescing wavelength range, then the fact that certain colours are perceived more strongly by the human eye than others is advantageously taken into account. Setting of corresponding distinctly wide wavelength ranges for fluorescence radiation can advantageously ensure a desired balance of the signal portions. It can also ensure that certain information about the examined tissue does not get lost and is preferably registered as reliably as it should.

Providing a device for illuminating within the meaning of the present invention, i.e. for exciting the tissue in question, in the handle of a drill or any other dental or endodontic tool, as is contemplated for certain embodiments according to the present invention, may advantageously increase a common manageability or use of the drill or tool and the monitoring system.

The use of radiation of corresponding LED and/or laser beams may advantageously dispense with having to resort to illumination filters. This may enable an advantageously straightforward design of the system according to the present invention, which is also achievable according to the present invention.

The use of radiation of corresponding LED and/or laser beams can, moreover, advantageously enable amplification of the illumination generated by the monitoring system. Shortcomings which may result for instance from illumination by means of halogen spotlights, which display a so-called "blue weakness", can thus be advantageously avoided.

The automatic interruption of a treatment, for instance of a tooth, by means of the treatment apparatus according to the present invention of certain embodiments can advantageously ensure that any undesirable treatment of a healthy or non-carious dental tissue is advantageously avoided.

The superimposition of results, which can be achieved by certain embodiments of the present invention, with illustrations known to the user of the system, for example white-light images, allows for superimposition of several pieces of information, which are respectively relevant per se, with the advantage of easier orientation.

Transferability of a or any filter or filter arrangement mentioned herein from a first position, in which it is not lying in an optical path and/or not acting as a filter, into a second position, in which it does filter, may advantageously enable the use of one and the same system without the need to change instruments in different applications to enable various pieces of information to be obtained.

More advantages may arise from the combination of the multiple or double bandpass filter with the surgery microscope here suggested for some embodiments according to the present invention. A surgery microscope is thus characterised by relatively large working distances, wherein a working distance means the distance between an object or tissue and the surface of the first lens lying in the optical path (seen from the object). Due to the relatively large working distances, daylight or ambient light always falls onto the object as well. Through the use and effect of a double or multiple bandpass filter in or on the surgery microscope, as suggested according to the present invention, fluorescence images can be created or achieved which are not—or only to a minimal extent—disturbed by daylight or ambient light falling laterally (because of the working distance).

Another advantage which ought to be stressed is that the tissue may be observed with the naked eye. Moreover, there is no need to take a picture of the tissue using a camera for assessing same later on. Rather, it is possible and provided for in certain embodiments according to the present invention that the tissue can be directly observed, i.e. without using a camera system.

BRIEF DESCRIPTION OF THE DRAWINGS

The present invention will be described below with reference to the appended drawing purely by way of example. In the drawing, identical reference numerals designate similar or identical elements. In the drawing.

FIG. 6 shows schematically simplified the basic idea of a double band filter having a combination of a long pass filter and a notch filter.

DETAILED DESCRIPTION OF THE INVENTION

Figure 1:
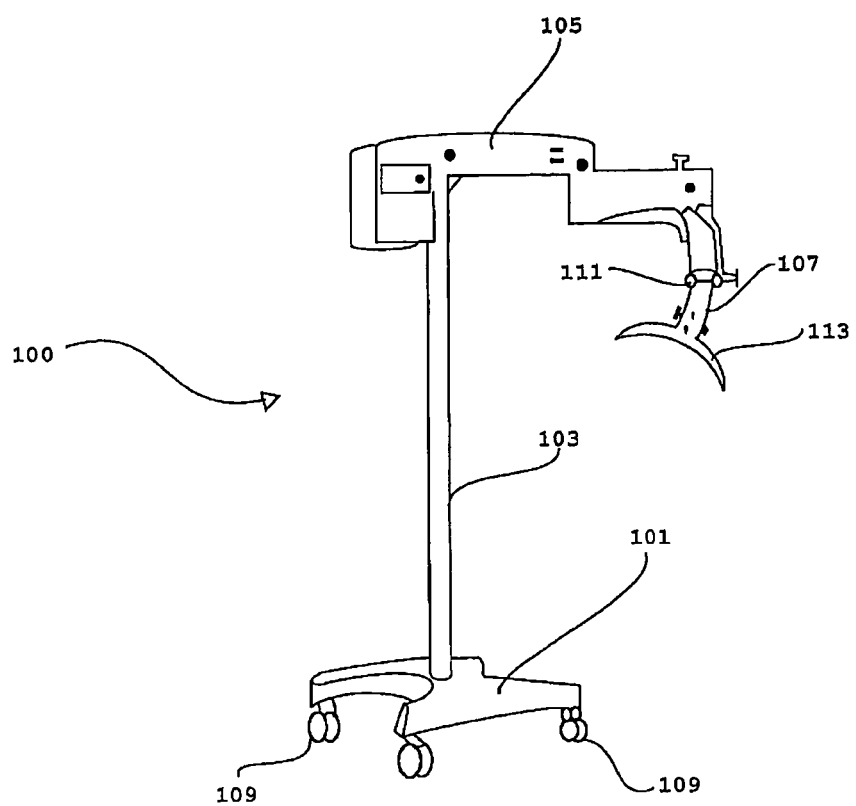
FIG. 1 shows an example of a monitoring system according to the present invention in overview.

FIG. 1 shows an example of a monitoring system according to the present invention 100 in overview. The monitoring system 100 is based on an extended surgery microscope OPMI Pico with S100 stative from the Carl Zeiss company, Germany. The monitoring system 100 has a foot 101, a stand 103 (maybe adjustable in height) and a superstructure 105 fitted with a microscope unit 107.

The foot 101 can include, as in the example of FIG. 1, two, three, four or more rollers 109 for ensuring the mobility of the monitoring system 100.

The microscopy unit 107 exhibits at least one ocular or two oculars 111, as shown by way of example in FIG. 1.

The microscopy unit 107 is adjustable by means of one or several joints in their three-dimensional orientation for the examiner.

The microscopy unit 107 includes for easy positionability in space at least one handle or—as shown by way of example in FIG. 1—two handles 113.

Figure 2:
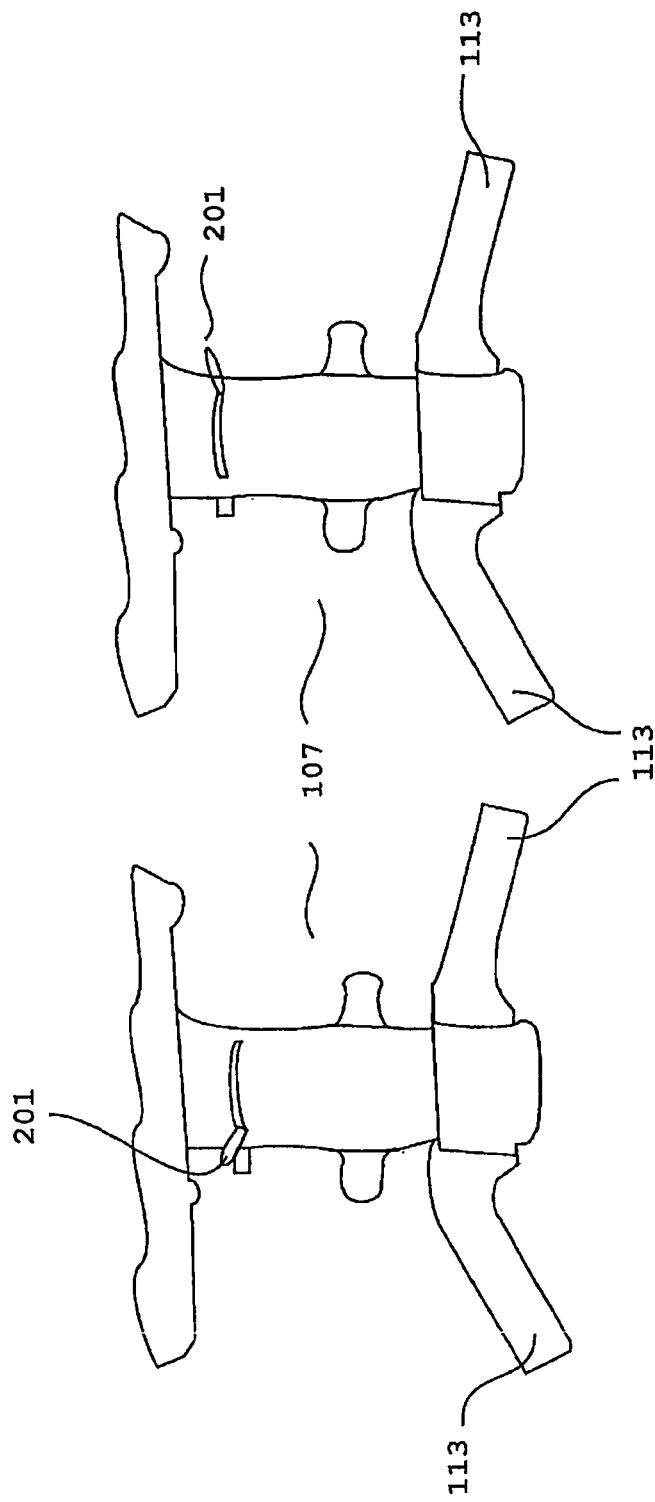
FIG. 2a shows the monitoring system according to the present invention of FIG. 1 with a filter snifter in a first position.
FIG. 2b shows the monitoring system according to the present invention of FIG. 1 with a filter snifter in a second position.

FIG. 2a shows the microscopy unit 107 of the monitoring system 100 according to the present invention in FIG. 1. The microscopy unit 107 comprises a filter snifter 200 which cannot be seen for illustration purposes in FIG. 1.

The filter snifter 200 can be pivoted by means of a pivot lever 201 between different positions, but at least between a first and a second position.

FIG. 2a shows the filter snifter 200 in the first position. In said first position, the filter(s) provided in or on the filter snifter 200 are swiveled into an optical path of the corresponding beam or light so that filtering takes place. Said swiveled-in mode corresponds to the first position of the filter snifter 200 illustrated in FIG. 2a.

The corresponding filter(s) can be observation filters, which are swiveled into the optical path of observation or into the detected beam or the detected light, i.e. into the optical path between the object or tissue being studied and the ocular.

Similarly, one or several illumination filters can be swiveled into or out of the corresponding illumination beam path by means of the filter snifter, which is illustrated in the figures, or by means of a filter snifter, non illustrated in the figures, in complement to, or alternately to, swiveling the observation filter(s), hence, into the optical path from the light source to the considered object or tissue.

Instead of the filter snifter 200 the device the monitoring system or the treatment apparatus according to the present invention may have any device that is configured to move one or more filters into the optical path or out of it. Swiveling is just one example. Any other movement is also encompassed by the present invention.

FIG. 2b shows, within the illustration of FIG. 2a, the microscopy unit 107 of the monitoring system 100 according to the present invention in FIG. 1, whereby the filter snifter 200 is in a second position, which can be seen, in comparison to FIG. 2a, from the position of the pivot lever 201. The pivot lever 201 can carry observation filters and/or illumination filters and swivel them along when it moves.

In the second position shown in FIG. 2b, the corresponding filters are swiveled out of the optical path so that no filtering takes place.

Figure 3:
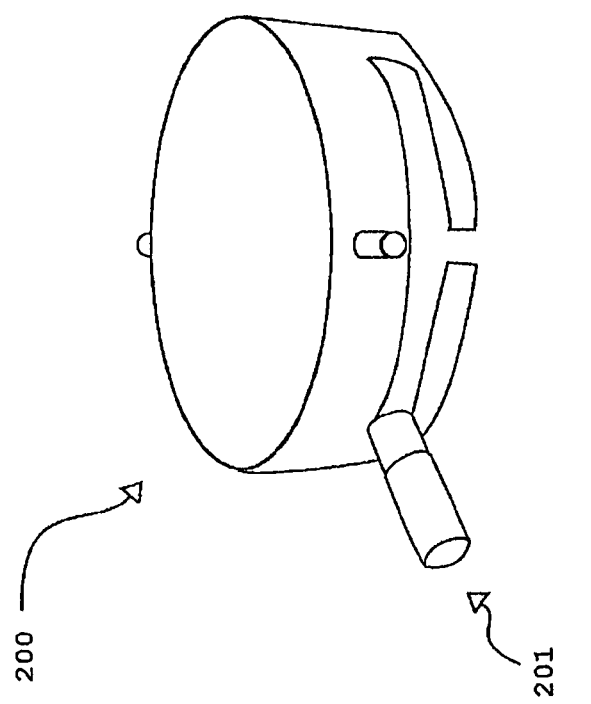
FIG. 3 shows the filter snifter of FIGS. 2a and 2b in isolated perspective representation.

FIG. 3 shows the filter snifter 200 of FIGS. 2a and 2b, schematically simplified, in isolated perspective representation.

Figure 4:
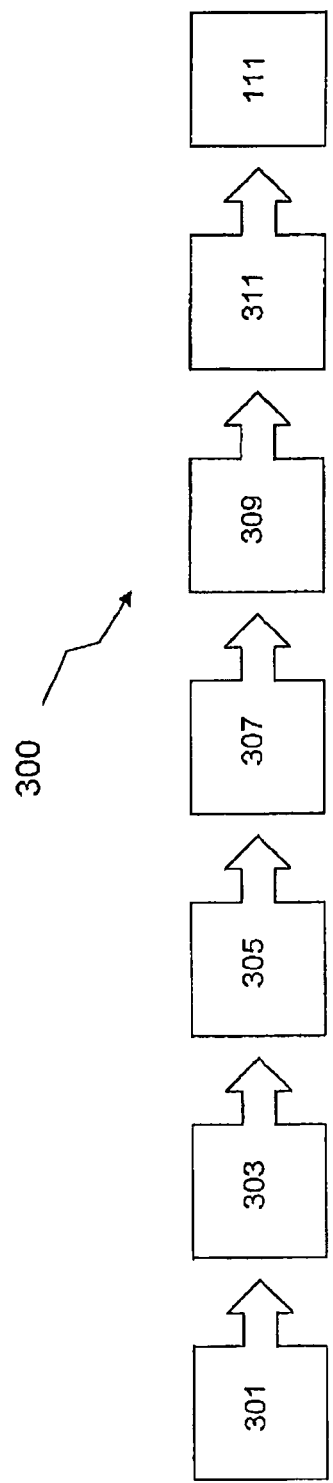
FIG. 4 shows as a block diagram schematically the assembly of the monitoring system according to the present invention of FIGS. 1, 2a and 2b.

FIG. 4 shows as a block diagram schematically an assembly 300 of the microscope unit 107 of the monitoring system according to the present invention of the previous figures. The block diagram shows the illumination optical path from the light source to the object or tissue, and the observation optical path from the object or tissue to the ocular of the microscopy unit 107.

The assembly 300 comprises a light source 301. Said source can be designed as a halogen radiator or spotlight or Xenon radiator or spotlight. It may, in addition, contain one or several LED or laser beams.

The illumination beam coming out of the light source 301 enters an optionally provided heat protection filter 303. A fibre optic or light conductor 305 is provided subsequent to the heat protection filter 303. The light exiting the heat protection filter is optionally filtered in an illumination filter 307. The illumination filter 307 is designed in some exemplary embodiments of the present invention as a short pass filter. The illumination filter 307 can be designed to let through light of the wavelength below 440 nm. The light passing through the illumination filter 307 hits a studied object, here a tooth 309. The fluorescence radiation emitted by the tooth 309 runs through an observation filter 311 and can be examined subsequently by the oculars 111. The observation filter can be a double bandpass filter. The light emitted by the tooth 309 or the fluorescence emitted therefrom can also be filtered with any other filter which the person skilled in the art may deem appropriate.

In this exemplary embodiment according to the present invention, the illumination filter 307 as well as the observation filter 311 can, respectively, independently of each other, be swiveled into the corresponding optical path or swiveled out of said path.

Figure 5:
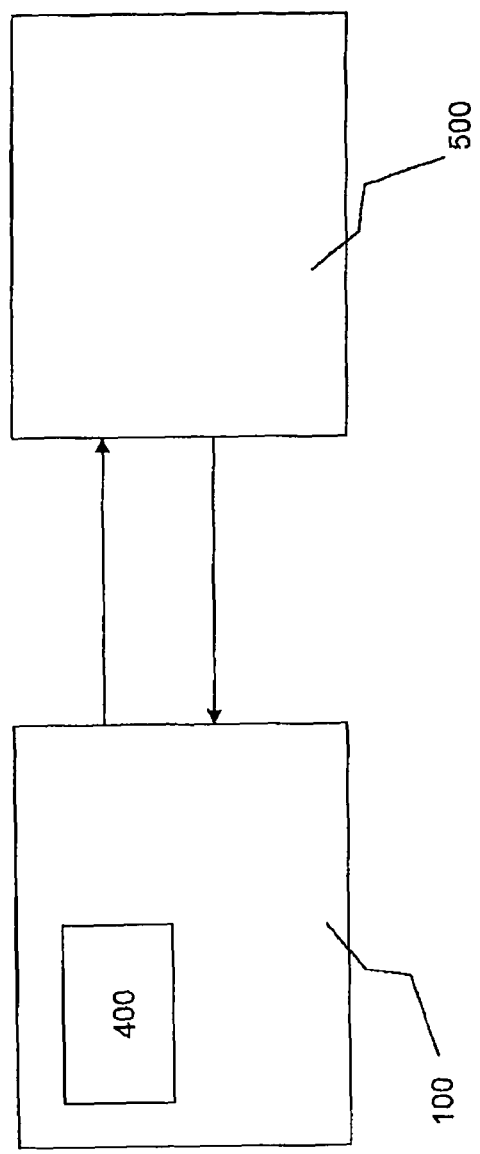
FIG. 5 shows schematically simplified a possible cooperation of the devices according to the present invention.

FIG. 5 shows, simplified, a possible cooperation of the devices according to the present invention, which are illustrated schematically and grossly simplified.

The monitoring system 100 includes a computing device 400 In the example of FIG. 5. The monitoring system 100 is in signal communication, as indicated by the arrows, with a treatment apparatus 500. The signal communication can be a single-direction control unit, or a reciprocally operating regulating unit.

It is noted that a computing device 400 according to the present invention can be in signal communication with regulating or control devices of the treatment apparatus 500 according to the present invention. This is not the case in other embodiments according to the present invention. In some embodiments according to the present invention, no computing device 400 according to the present invention is provided.

FIG. 6 shows in a simplified diagram the basic idea of a double band filter, which is a combination of only one long pass filter and one notch filter.

Thereby, the reference sign 601 designates the transmission function of the notch filter, 602 designates the transmission function of the long pass filter and 603 designates the total transmission function of the double band filter described with reference to FIG. 6.

REFERENCE NUMERALS

100 Monitoring system
101 Foot
103 Stand
105 Superstructure
107 Microscopy unit
109 Rollers
111 Oculars
113 Handles
200 Filter snifter
201 Pivot lever
300 Assembly
301 Light source
303 Heat protection filter
305 Fibre optics
307 Illumination filter
309 Tooth
311 Observation filter
400 Computing device
500 Treatment apparatus
601 Transmission function of the notch filter
602 Transmission function of the long pass filter
603 Total transmission function

What is claimed is:

1. A method for examining biological tissue, wherein the method comprises:
illuminating the biological tissue to be examined by illumination radiation emitted by a light source along an illumination optical path to cause the biological tissue to emit fluorescence radiation;
filtering the emitted fluorescence radiation by a filter positioned in an observation optical path to generate an image of the biological tissue based on the filtered fluorescence radiation, which image is capable of at least one of (i) being observed and (ii) being recorded and optically displayed;
the filter being a double bandpass filter comprising a combination of a longpass filter and a notch filter and having a first passband within a wavelength range of from 460 nm to 560 nm and a second passband within a wavelength range of from 600 nm to 685 nm, the first passband and the second passband being apart from one another by at least 60 nm.

2. The method of claim 1, wherein the illumination radiation has a wavelength within a wavelength range of from 370 nm to 440 nm.

3. The method of claim 1, wherein the method further comprises moving the filter in and out of the observation optical path.

4. The method of claim 1, wherein the observation optical path is that of a surgical microscope.

5. The method of claim 1, wherein the first passband is narrower than the second passband.

6. The method of claim 1, wherein the first passband extends from 500 nm to 520 nm, overlaps therewith or lies within that range.

7. The method of claim 1, wherein the second passband extends from 614 nm to 685 nm, overlaps therewith or lies within that range.

8. The method of claim 6, wherein the second passband extends from 614 nm to 685 nm, overlaps therewith or lies within that range.

9. The method of claim 1, wherein the notch of the notch filter is superimposed in a wavelength range within which the longpass filter has a high transmission.

10. The method of claim 1, wherein the method further comprises interrupting an operation of a treatment device based on an evaluation of an intensity of the filtered fluorescence radiation.

11. The method of claim 1, wherein the method is used for determining the presence or absence of tooth decay or carries.

12. The method of claim 1, wherein the generated image is capable of being observed.

13. The method of claim 1, wherein the generated image is capable of being recorded and displayed.

14. An apparatus for examining biological tissue, wherein the apparatus comprises:
a light source which provides illumination radiation for illuminating an object;
an illumination optical path from the light source to the object;
at least one of an ocular for viewing an image of the illuminated object and a camera for recording an image of the illuminated object;
an observation optical path from the object to the at least one of an ocular and a camera;
a filter positioned in the observation optical path, which filter is a double bandpass filter comprising a combination of a longpass filter and a notch filter and having a first passband within a wavelength range of from 460 nm to 560 nm and a second passband within a wavelength range of from 600 nm to 685 nm, the first passband and the second passband being apart from one another by at least 60 nm.

15. The apparatus of claim 14, wherein the apparatus further comprises a filter snifter capable of assuming a first snifter position in which the filter is positioned in the observation optical path and a second snifter position in which the filter is positioned outside the observation optical path.

16. The apparatus of claim 14, wherein the light source emits illumination radiation within a wavelength range of from 370 nm to 440 nm.

17. The apparatus of claim 14, wherein the light source emits illumination radiation within a wavelength range of from 398 nm to 440 nm.

18. The apparatus of claim 15, wherein the light source emits illumination radiation within a wavelength range of from 370 nm to 440 nm.

19. The apparatus of claim 18, wherein the light source emits illumination radiation within a wavelength range of from 398 nm to 440 nm.

20. The apparatus of claim 14, wherein the first passband is narrower than the second passband.

21. The apparatus of claim 14, wherein the first passband extends from 500 nm to 520 nm, overlaps therewith or lies within that range.

22. The apparatus of claim 14, wherein the second passband extends from 614 nm to 685 nm, overlaps therewith or lies within that range.

23. The apparatus of claim 14, wherein the notch of the notch filter is superimposed in a wavelength range within which the longpass filter has a high transmission.

24. The apparatus of claim 14, wherein the apparatus comprises an ocular for viewing an image of the object.

25. The apparatus of claim 14, wherein the apparatus comprises a camera for recording an image of the object.

26. The apparatus of claim 18, wherein the apparatus is a surgical microscope comprising a microscope unit with at least one ocular unit and an adjustable stand.

27. The apparatus of claim 18, wherein the apparatus is a digital microscope comprising a camera for recording a generated image based on filtered fluorescent radiation emitted by the object in response to being illuminated by light from the light source and a display unit for displaying the recorded image.

28. A treatment system, wherein the system comprises a treatment device, a control for the treatment device, and the apparatus of claim 14, the apparatus being in signal communication with the control for the treatment device.

29. The system of claim 28, wherein the light source of the apparatus emits illumination radiation within a wavelength range of from 370 nm to 440 nm.

* * * * *